United States Patent [19]

Koser et al.

[11] Patent Number: 4,513,137

[45] Date of Patent: Apr. 23, 1985

[54] IODONIUM SALTS

[75] Inventors: Gerald F. Koser, Munroe Falls; Carol S. Carman, Alliance, both of Ohio

[73] Assignee: The University of Akron, Akron, Ohio

[21] Appl. No.: 252,327

[22] Filed: Apr. 9, 1981

[51] Int. Cl.$^3$ ............................................ C07D 213/26
[52] U.S. Cl. ....................................... 546/14; 546/255; 546/266; 546/267; 546/339; 546/340; 546/347; 548/146; 548/215; 548/217; 548/235; 548/400; 548/570; 548/571; 548/110; 548/406; 549/3; 549/41; 549/43; 549/50; 549/81; 549/214; 549/460; 556/430; 556/432; 556/447; 556/449; 556/465; 424/263; 424/275; 424/278; 424/272; 424/274; 424/184; 424/270
[58] Field of Search ............... 549/5, 214; 260/346.11, 260/347.2, 347.3, 347.7, 347.8; 556/427, 428, 430, 447, 449, 465, 482, 485

[56] References Cited

U.S. PATENT DOCUMENTS

| | | | |
|---|---|---|---|
| 3,010,967 | 11/1961 | Siegrist et al. | 260/346.11 |
| 3,622,586 | 11/1971 | Jezic | 260/295 |
| 3,712,929 | 1/1973 | Jezic | 260/332.5 |
| 3,734,928 | 5/1973 | Jezic | 260/332.5 |
| 3,759,989 | 9/1973 | Jezic | 260/539 |
| 3,896,140 | 7/1975 | Plepys et al. | 260/307 |
| 3,952,028 | 4/1976 | Jezic | 260/350 |

OTHER PUBLICATIONS

"Organic Chemistry", Nitrogen, Sulfur, and Phosphorus, Kemp & Vellacio, p. 1234.
"Organic Chemistry", Heterocyclic Compounds, Morrison & Boyd, 4th Ed., 1983, Allyn & Bacon, p. 1267.
"Basic Principles of Organic Chemistry", Heterocyclic Aromatic Compounds, Roberts & Caserio, pp. 967, 968.
EPA Report, algicidal activity, CA, 84, 100689j, (1976).

*Primary Examiner*—Henry R. Jiles
*Assistant Examiner*—Robert C. Whittenbaugh
*Attorney, Agent, or Firm*—Oldham, Oldham & Weber Co.

[57] ABSTRACT

Mono- or bis(iodonium salts) are produced in neutral organic solvents by the reaction of an [hydroxy (organosulfonyloxy)iodo]arene with a bis(triorganosilyl)arene, a bis(trihalosilyl)arene, or with a mono- or bis(triorganosilyl)heterocyclic compound, or a mono- or bis(-trihalosilyl)heterocyclic. The iodonium salts are made under conditions of regiospecific control.

20 Claims, No Drawings

IODONIUM SALTS

TECHNICAL FIELD

The present invention relates to the preparation of mono- or bis(iodonium salts) in neutral organic solvents, by the reaction of a Hosia compound with a bis(triorganosilyl)arene, or a bis(trihalosilyl)arene, or a mono- or bis(triorganosilyl)heterocyclic, or a mono- or bis(trihalosilyl)heterocyclic.

BACKGROUND ART

The compound [hydroxy(tosyloxy)iodo]benzene is known but is a relatively new compound having first been reported in 1970.

U.S. Pat. No. 3,712,920 relates to 2,5-thiophenediyl-bis(iodonium salts) produced by a condensation reaction in the presence of sulfuric acid. It is essential to employ at least a 100 percent molar excess of sulfuric acid. The reactants are a phenyl-2-thienyliodonium trifluoroacetate and a (diacetoxyiodo)benzene. This patent is not pertinent in that not only are the reactants clearly different, but also the reaction must be carried out in a sulfuric acid which limits the types of acid-sensitive substituted groups which may be utilized in the reaction.

U.S. Pat. No. 3,734,928 relates to difunctional iodonium salts of diphenyl oxide. Generally, the compounds are prepared by the condensation of (diacetoxyiodo)-phenyl ether with thiophene or benzene in the presence of trifluoroacetic acid. This patent also contains no suggestion of the reactants of the present invention.

U.S. Pat. No. 3,759,989 relates to a bis(p-phenoxyphenyl)iodonium trifluoroacetate or trichloroacetate salts. U.S. Pat. No. 3,896,140 relates to 3,5-dimethyl-4-isoxazolyliodonium salts of the formula set forth therein. Similarly, U.S. Pat. No. 3,952,028 relates to bis(dichloroacetoxy)iodobenzenes and bis(trichloroacetoxy)iodobenzenes having the formula set forth therein. U.S. Pat. No. 3,622,586 relates to pyridyliodonium salts of the formula set forth therein. All patents lack the reactants of the present invention, and generally relate to acid catalyzed condensations.

The above patents also failed to suggest any reaction of bis(trihalosilyl)arenes, or bis(triorganosilyl)arenes, or of mono- or bis(triorganosilyl)heterocyclics, or mono- or bis(trihalosilyl)heterocyclics, as well as the mono- or bis(iodonium salts) of the present invention.

DISCLOSURE OF INVENTION

It is therefore an object of the present invention to produce mono- or bis(iodonium salts) in neutral organic solvents.

It is a further object of the present invention to produce mono- or bis(iodonium salts), as above, by the reaction of [hydroxy(organosulfonyloxy)iodo]arenes with bis(trihalosilyl)arenes, bis(triorganosilyl)arenes, or mono- or bis(triorganosilyl)heterocyclics, or mono- or bis(trihalosilyl)heterocyclics.

It is still another object of the present invention to produce mono- or bis(iodonium salts), as above, wherein good yields are obtained.

It is yet another object of the present invention to produce mono- or bis(iodonium salts), as above, wherein said reactants contain acid sensitive groups which remain intact.

It is yet another object of the present invention to produce mono- or bis(iodonium salts), as above, wherein mono- or bisiodonium salts can be produced under conditions of regiospecific control.

It is yet another object of the present invention to produce mono- or bis(iodonium salts), as above, wherein the mono- or bis(iodonium salts) can be produced under reflux conditions.

These and other objects of the present invention will become apparent from the following specification.

In general, an iodonium salt comprises a compound having the formula

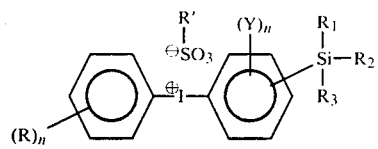

or the formula

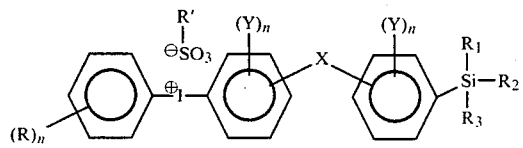

where n of $(R)_n$ is from 1 to 5, where $(R)_n$ can be the same or different, and where R is a halo, an H, a hydrocarbon group, a hetero atom substituted hydrocarbon group, a heterocyclic, a halo substituted hydrocarbon, and combinations thereof;

where R' is a hydrogen, a halo, a hydrocarbon group, a hetero atom substituted hydrocarbon group, a halo substituted hydrocarbon group, and combinations thereof;

where n of $(Y)_n$ is from 1 to 4, where Y is the same or different, and where Y is hydrogen, halo, a hydrocarbon group, a hetero group, and combinations thereof;

where $R_1$, $R_2$, and $R_3$ can be the same or different, wherein $R_1$, $R_2$, and $R_3$ are a hydrogen, a hydrocarbon group, a halo, an oxygen substituted hydrocarbon group, and combinations thereof;

wherein X is a carbon-carbon bond, a hydrocarbon group, Si, a hydrocarbon substituted Si; O, NH, S, Si, Sn, SO, $SO_2$, a nitrogen substituted hydrocarbon group, an oxygen substituted hydrocarbon group, an organo $Si_n$ group where n is from 1 to 10, a $Si_n$ group where n is from 1 to 10, and combinations thereof.

In general, a process for preparing an iodonium salt, comprises the steps of:

obtaining a compound having the formula

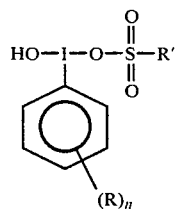

where R' is hydrogen, a halo, a hydrocarbon group, a hetero atom substituted hydrocarbon group, a halo substituted hydrocarbon group, and combinations thereof;

where n of $(R)_n$ is from 1 to 5, where R can be the same or different, and where R is a halo, an H, a hydrocarbon group, a hetero atom substituted hydrocarbon group, a heterocyclic, a halo substituted hydrocarbon, and combinations thereof;

adding a sufficient amount of a compound having the formula

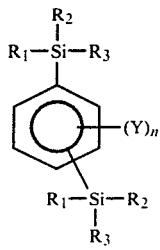

or the formula

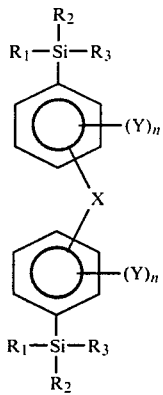

wherein $R_1$, $R_2$, and $R_3$ can be the same or different, wherein $R_1$, $R_2$, and $R_3$ are a hydrogen, a hydrocarbon group, a halo, an oxygen substituted hydrocarbon group, and combinations thereof;

wherein $(Y)_n$ is from 1 to 4, where Y is the same or different, and where Y is hydrogen, halo, a hydrocarbon group, a hetero group, and combinations thereof;

where X is a carbon-carbon bond, a hydrocarbon group,

a hydrocarbon substituted Si; O, NH, S,

SO, $SO_2$, a nitrogen substituted hydrocarbon group, an oxygen substituted hydrocarbon group, an organo $Si_n$ group where n is from 1 to 10, a $Si_n$ group where n is from 1 to 10, and combinations thereof; and reacting said compounds in the neutral organic solvent to form an iodonium salt wherein at least one of said

group has been replaced by said reactant.

In general, an iodonium salt, comprises:
a compound having the formula

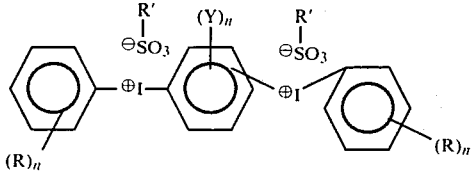

or the formula

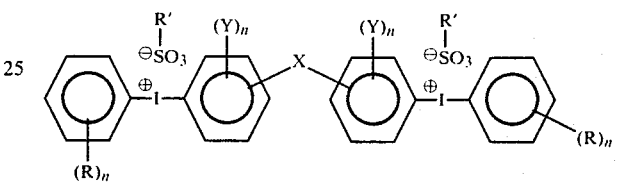

where n of $(R)_n$ is from 1 to 5, where R can be the same or different, and where R is a halo, an H, an hydrocarbon group, a hetero atom substituted hydrocarbon group, a heterocyclic, a halo substituted hydrocarbon, and combinations thereof;

where R' is a hydrogen, a halo, a hydrocarbon group, a hetero atom substituted hydrocarbon group, a halo substituted hydrocarbon group, and combinations thereof;

where n of $(Y)_n$ is from 1 to 4, where Y is the same or different, and where Y is hydrogen, halo, a hydrocarbon group, a hetero group, and combinations thereof; and wherein X is a carbon-carbon bond, a hydrocarbon group,

a hydrocarbon substituted Si; O, NH, S,

SO, $SO_2$, a nitrogen substituted hydrocarbon group, an oxygen substituted hydrocarbon group, an organo $Si_n$ group where n is from 1 to 10, a $Si_n$ group where n is from 1 to 10, and combinations thereof.

In general, an iodonium salt, comprises:
a compound having the formula

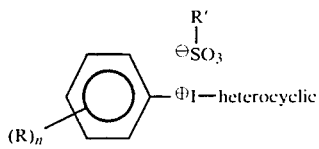

or a compound having the formula

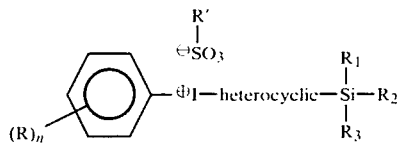

or a compound having the formula

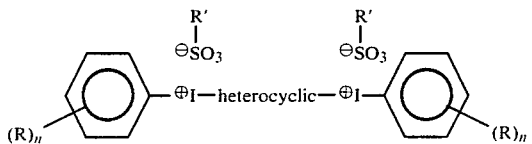

where n of $(R)_n$ is from 1 to 5, R can be the same or different, and where R is a halo, an H, a hydrocarbon group, a hetero atom substituted hydrocarbon group, a heterocyclic, a halo substituted hydrocarbon, and combinations thereof;

where R' is a hydrogen, a halo, a hydrocarbon group, a hetero atom substituted hydrocarbon group, a halo substituted hydrocarbon group, and combinations thereof;

where $R_1$, $R_2$, and $R_3$ can be the same or different, and wherein $R_1$, $R_2$, and $R_3$ are a hydrogen, a hydrocarbon group, a halo, an oxygen substituted hydrocarbon group, and combinations thereof; and wherein said HETEROCYCLIC compound is substituted with at least one compound, said compound being hydrogen, a hydrocarbon group, or a halo.

In general, a process for making an iodonium salt, comprises the steps of:

obtaining a compound having the formula

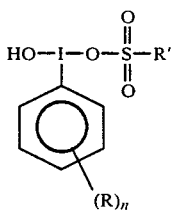

where R' is is a hydrogen, a halo, a hydrocarbon group, a hetero atom substituted hydrocarbon group, a halo substituted hydrocarbon group, and combinations thereof;

and where n of $(R)_n$ is from 1 to 5, where R can be the same or different, and where R is a halo, an H, a hydrocarbon group, a hetero atom substituted hydrocarbon group, a heterocyclic, a halo substituted hydrocarbon, and combinations thereof;

adding a sufficient amount of a mono- or a bis(triorganosilyl)heterocyclic compound or a mono- or bis(trihalosilyl)heterocyclic to cause a reaction;

reacting said compounds in a neutral organic solvent to form an iodonium compound wherein at least one of said

group has been replaced by said reactant.

BEST MODE FOR CARRYING OUT THE INVENTION

The starting compounds for the preparation and production of the Hosia compounds are ring-substituted [hydroxy(organosulfonyloxy)iodo]arenes having the formula

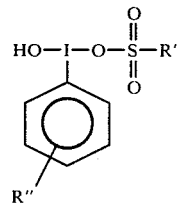

FORMULA NO. 1 wherein R' is a hydrogen or an alkyl having from 1 to 20 carbon atoms, desirably from 1 to 10 carbon atoms. R' may also be an aryl containing from 6 to 40 carbon atoms, preferably from 6 to 20 carbon atoms. R' can also be a haloaryl having from 6 to 40 carbon atoms, etc., wherein the halogen atom is attached either to the benzene ring or to an alkyl substituent of the haloaryl group. R' can further be an aryl (6 to 40 carbon atoms) group substituted with hetero atom substituents (that is other than carbon), for example $NO_2$, CN, COOH, CHO, alkoxy groups having from 1 to 6 carbon atoms, aryloxy groups having from 6 to 30 carbon atoms, and the like. By the term aryl, it is meant any aromatic radical in which one or more ring positions can be substituted with an alkyl, an aromatic, an alkyl substituted aromatic, or an aromatic substituted alkyl. Preferred R' groups include the aryls and the halo substituted aryls. Examples of specific R' groups include methyl, ethyl, propyl, isopropyl, butyl, phenyl, p-tolyl, p-cumyl, alpha or beta naphthyl, and the like. R'' groups include hydrogen or alkyl having from 1 to 5 carbon atoms and attached ortho, meta, or para to the indicated ring. A highly preferred group is o-methyl since it has been found to increase the solubility of the formula 1 compound. Preferred formula 1 compounds include [hydroxy(tosyloxy)iodo]benzene and [hydroxy(tosyloxy)iodo]o-methylbenzene. It is important that the formula set forth above contains a sulfonyloxy group in order to permit ligand transfer.

The other reactant is an iodoarene generally indicated by the formula

FORMULA 2

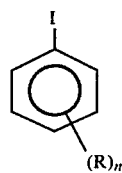

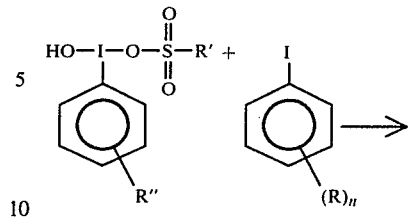

FORMULA NO. 3

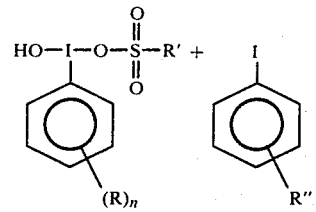

Unless otherwise noted, n may be from 1 to 5 groups, preferably 1 or 2 groups, and thus R is attached at any or all of the available ring positions, for example, ortho; meta; para; meta and para; meta, ortho and para; and the like. The R groups can be the same or different. Moreover, R can be a benzo group, for example 2,3- or 3,4-benzo; or hydrogen. The R group can also be a halogen, for example, fluoro, chloro, iodo, or bromo. The R group can be an alkyl having from 1 to 20 carbon atoms, desirably 1 to 10 carbon atoms, and preferably from 1 to 5 carbon atoms. Specific examples include ethyl, methyl, propyl, isopropyl, butyl, and the like. Furthermore, cycloalkyl groups may be utilized in the present invention having from 3 to about 20 carbon atoms, desirably from about 3 to about 10 carbon atoms, and preferably 3 to 5 carbon atoms. Specific examples include cyclopropyl, cyclobutyl, cyclopentyl, cyclohexyl, and the like. Additionally, R can be an aryl group, as defined above, having from 6 to 40 carbon atoms, preferably 6 to 20 carbon atoms, and preferably is attached at the meta or para position. Examples of specific aryl groups include phenyl, tolyl, cumyl, and the like. Similarly, R can be a halogen substituted aryl (6 to 40 carbon atoms, etc.) group having various halogens such as fluoro, chloro, iodo, or bromo, wherein the halogen atom is attached either to the benzene ring or to an alkyl substituent of the aryl group. R also includes alpha- or beta-naphthyl as well as the alkyl, the halo, and the cycloalkyl substituted naphthyls, with the substituent attached at either the alpha or beta position. The alkyl, halogen, or cycloalkyl substituents thereon are the same as the compounds set forth above, for example, the alkyl can have from 1 to 20 carbon atoms, the cycloalkyl can have from 3 to 20 carbon atoms, and the like. Additionally, R can be aryl groups (6 to 40 carbon atoms, etc.) substituted with hetero atom substituents (that is, other than carbon). For example, nitro ($NO_2$) groups, nitroso (NO) groups, cyano (CN) groups, carboxyl groups (COOH), aldehydo (CHO), hydroxy (OH), alkoxy groups having from 1 to 5 carbon atoms, aryloxy groups having from 6 to 30 carbon atoms, and the like. Still further examples of compounds which fit the above-noted general description include pyridinyl, alpha or beta furyl, alpha or beta thienyl, and the like.

Of the above numerous R groups, the alkyl, the aryl, and the halo are preferred.

By transfer of the hydroxy and the specific sulfonyl oxyligand from the iodine III atom of the formula number 1 molecule to the iodine I atom of the formula number 2 molecule, a product is produced as represented by formula number 3.

R', R", and $(R)_n$ are as set forth above.

The reaction occurs in relatively neutral organic solvents, for example, solvents having a pH of from about 4 to about 9, and preferably from about 5 to about 8. Thus, R can be many groups which otherwise the use of acid medium would prohibit. Examples of mild solvents include dichloromethane (preferred), acetonitrile, acetic acid, chloroform, and the like, and also dipolar aprotic solvents such as dimethylsulfoxide, dimethylformamide, and the like. Neutral organic solvents are known to those skilled in the art. Reactions can take place at ambient temperature. Generally, the reaction temperature will range from slightly above the freezing point of the solvent to about the boiling point of the solvent. Generally, the reaction temperature ranges from about 0° C. to about 100° C. with from about 15° C. to about 80° C. being preferred. The pressure is generally atmospheric although it can range from about 0.2 to about 5 atmospheres. Usually, the best yields have been obtained at room temperature. Yield of the desired product is often in excess of 70 or 80 percent. In order to ensure a good yield of the Hosia compound, the mole ratio of the iodoarene to the compound of formula 1 generally ranges from about 0.8 to about 4.0 and preferably is about 1.0.

The Hosia compounds, as represented by formula number 3, generally have antimicrobial properties. Hence, they can be utilized in situations, as set forth hereinbelow.

It is a further aspect of the present invention to react the Hosia compound (#3) with either a bis(triorganosilyl)arene or a bis(trihalosilyl)arene, that is respectively "BTOSA" or "BTHSA" in neutral solvents to yield mono- or bis(iodonium salts). The use of neutral organic solvents permits synthesis of iodonium salts bearing acid sensitive groups. The process permits the regiospecific synthesis of mono- or bis-iodonium salts with the iodine atom of the Hosia compound being introduced at the point of attachment of the silicon atom in the silane precursor. The BTOSA and BTHSA compounds are generally indicated by the formulae

FORMULA 4    FORMULA 5

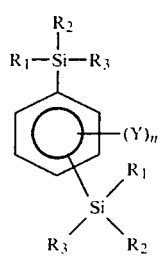
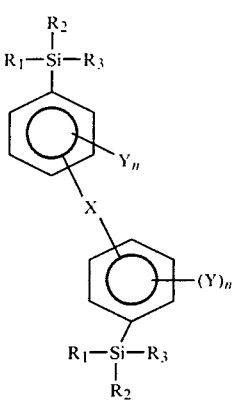

It is noted that the benzene ring of formula 4 can also be a naphthalene group.

$R_1$, $R_2$, and $R_3$ can be the same or different groups. Moreover, the two Si-$R_1$, $R_2$, $R_3$ groups can be the same or different. $R_1$, $R_2$, and $R_3$ can be hydrogen or an alkyl having from 1 to 5 carbon atoms. Specific examples of alkyl groups include methyl, ethyl, propyl, butyl, and the like. $R_1$, $R_2$, and $R_3$ can also be halo, that is fluoro, chloro, iodo, or bromo. They can also be aryl groups having from 6 to 24 carbon atoms, with 6 to 12 carbon atoms being preferred. Yet another group is the alkoxy having from 1 to 5 carbon atoms with specific examples including methoxy, ethoxy, and the like. Preferred $R_1$, $R_2$, and $R_3$ groups include methyl, chloro, phenyl, and the like.

An important aspect of the present invention is that compounds 4 and 5 require a silicon substituent so that electrophilic bond cleavage between the arene carbon atom and the silicon atom by Hosia compounds occurs resulting in the production of the iodonium salt.

The X compound as shown in formula number 5 can be any of several different groups. For example, X can be O, NH,

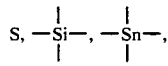

SO, SO$_2$,

and the like. X can also be N—R''' where R''' is an alkyl having from 1 to 5 carbon atoms, preferably methyl, or an aryl having from 6 to 12 carbon atoms, and preferably is phenyl. The N—R''' group is preferably located para to both adjacent phenyl groups. X can also be $-(CH_2)_n-$ where n is from 0 to 10, and preferably 0, 1, or 2. X can also be the following compounds

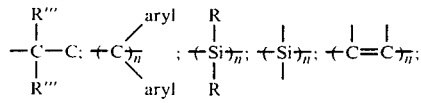

wherein n is from 1 to 10, preferably 1. X can also be

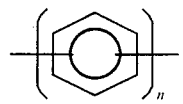

Preferably X is O, NH, S, or $-(CH_2)_n-$ where n is 0 to 10, preferably 0, 1, or 2.

As shown in formulas 4 and 5 above, the ring can be substituted with $(Y)_n$ groups where n is from 1 to 4 groups; that is, of the four available ring positions, 1, 2, 3, or all four of them can contain a Y group where Y can be the same or different. Preferably, the ring is not substituted, that is Y is hydrogen. The Y group can be an alkyl having from 1 to 5 carbon atoms, an aryl having from 6 to 12 carbon atoms, a halo, or a heterogeneous group such as NO$_2$, CN, COOH, CHO, or OH. The various substituted Y groups can also be the same or different. Moreover, the Y group or groups on one ring compound can be the same or different as the Y groups on the other ring compound.

A preferred compound of formula number 4 is 1,2-, 1,3-, or 1,4-bis(trimethylsilyl)benzene, and the like. Examples of preferred compounds represented by formula number 5 include 4,4'-bis(trimethylsilyl)biphenyl, 4,4'-bis(trimethylsilyl)diphenylether, and the like.

The product obtained when compounds as represented by formula 3 and formula 4 are reacted together in a neutral solvent is as follows:

FORMULA 3

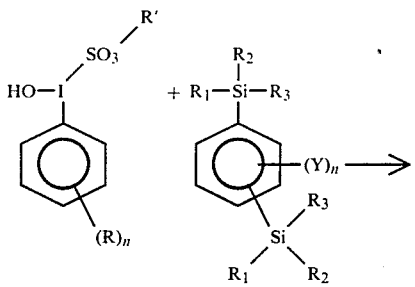

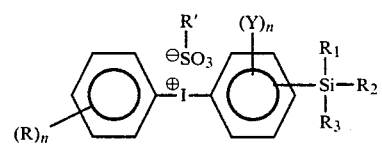

As apparent from formula 6, many numerous types of mono-iodonium salts containing a silane group therein can be produced. Examples of specific salts include phenyl(4-trimethylsilylphenyl)iodonium-p-toluenesulfonate, and the like.

The reaction of a compound as set forth in formula 3 with compound 5 as set forth in formula 5 is as follows:

FORMULA NO. 3    FORMULA NO. 5

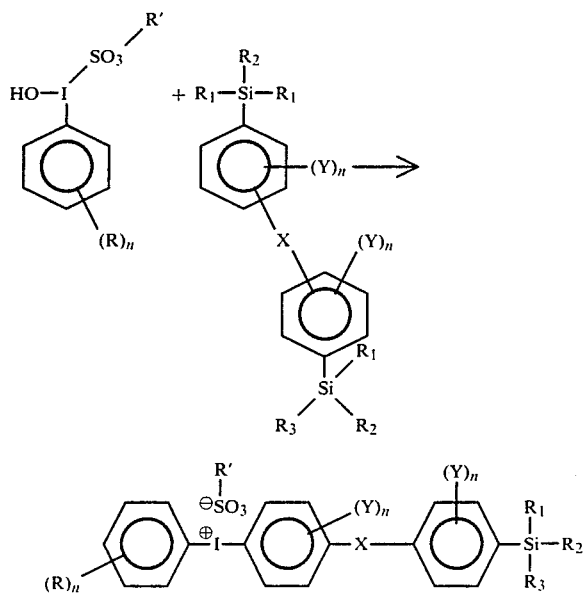

FORMULA NO. 7 where $(R)_n$, R'. X, $(Y)_n$, and $R_1$, $R_2$, and $R_3$ are as set forth above. Examples of specific compounds as set forth by formula 7 include 4-trimethylsilyl-4'-phenyliodoniodiphenyl ether p-toluenesulfonate; 4-trimethylsilyl-4'-phenyliodoniodiphenyl sulfide p-toluenesulfonate, and the like.

Additionally, it has been found that the monoiodonium salt as represented by formulas 6 and 7 can be further reacted with Hosia compounds as set forth in formula 3 whereby the bond between the silicon atom and the carbon atom is cleaved with the Hosia compound being substituted therefor minus the hydroxy group. This results in a formation of bis(iodonium salts). The type and formulation of the bis(iodonium salts) are thus numerous, especially considering the different types of groups $(R)_n$, R', $(Y)_n$, X, $R_1$, etc., can be.

The reactions to produce the compounds indicated by formulas 6 and 7 as well as the production of the bisiodonium salts are the same as previously set forth hereinabove and thus is hereby fully incorporated. That is, as with the reaction between formula number 1 and the iodoarene compounds of formula number 2 to yield a Hosia compound of formula number 3, the present reactions also occur in a neutral organic solvent. Moreover, the other reaction parameters such as the pressure, and the like are the same as set forth above and is thus hereby incorporated.

The amount of the BTOSA or the BTHSA compounds, that is compounds represented by formulas 4 or 5, to the Hosia compounds, formula 3, on a mole ratio is usually a slight excess, that is from about 0.8 to about 5, desirably from about 0.9 to about 2, and preferably from about 1 to 1, that is a mole ratio of 1.0. The reaction can be carried out under reflux conditions to improve yield. Generally, the pressure is atmospheric, although the reaction can be carried out under vacuum or pressure, if desired. Nitrogen, helium, etc., can be utilized in lieu of air in the reaction vessel. The non-acid reaction route permits compounds (formulas 6 and 7) to be made under regiospecific conditions by selecting the appropriate BTOSA or BTHSA compound (formulas 4 and 5) as well as the appropriate Hosia compound (formula 3).

The various iodonium salts (formulas 6 and 7) formed according to the present invention have a relatively high toxicity to a broad spectrum of bacteria, fungi, yeast, and small RNA viruses. Moreover, such salts have low toxicity to terrestrial plants and may therefor be applied in bactericidal amounts to obtain excellent control of microbial organisms which attack seeds, roots, or above-ground portions of such plants. Moreover, such compounds in possessing antimicrobial properties can be utilized in adhesives, cooling water, inks, plasticizers, resins, polymer materials, greases, detergents, soap, shampoos, oils, paints (such as latex paints), and the like, to prevent mold and mildew. The compounds of the present invention may further be used in textiles, fabrics, paper, or other cellulosic products and further may be employed in the impregnation of wood, lumber, wallboard, plaster, and the like to prevent attack of bacteria organisms of rot, mold, mildew, and decay. Still further applications of the various iodonium salts of the present invention include spermicides, in stunting the growth and enhancing the maturation of plants, photoinitiators of cationic polymerizations, as a component in a photosensitive admixture, in the selective inhibition of microbial deamination in ruminant animals; in the addition to feed of nonruminants to stimulate growth, in improving feed utilization, in preventing diarrhea; and in preventing tartar buildup on teeth.

In lieu of the BTOSA and BTHSA compounds, formulas 4 and 5, numerous heterocyclic compounds, whether containing a mono- or a disubstituted silane group thereon can be utilized. The various heterocyclic compounds are well known and representative compounds can be found in the literature, e.g., the Handbook of Chemistry and Physics. Examples of specific heterocyclic compounds which include furan (Compound A), thiophene (Compound B), dibenzofuran Compound C), dibenzothiophene (Compound D), benzofuran (Compound E), benzothiophene (Compound F), isobenzofuran (Compound G), thiophthene (Compound H), thieno[3,2-b]thiophene (Compound I), oxazole (Compound J), thiazole (Compound K), benzoxazole (Compound L), pyrrole (Compound M), and pyridine (Compound N). Of these compounds, furan, pyrrole, thiophene and pyridine are preferred. These heterocyclic compounds, as noted, can contain a single silane group thereon, that is

groups where $R_1$, $R_2$, and $R_3$ are various groups as set forth hereinabove. $R_1$, $R_2$, or $R_3$ can be the same or dissimilar. Moreover, the various heterocyclic compounds can contain two silane groups thereon. Each of the silane groups can be identical to each other or different. The mono- or disubstituted silane groups will generally be substituted at any point on the ring where a double bond exists. Thus, a great number of reactive heterocyclic compounds exist. The various heterocyclic compounds preferably are not substituted. However, they can contain substituted groups such as an alkyl group containing from 1 to 5 carbon atoms with methyl being preferred, a halo group such as fluoro, chloro, iodo, or bromo, with chloro being preferred, or an aryl group containing from 6 to 18 carbon atoms, with 6 to 12 carbon atoms being preferred. The heterocyclic compounds can contain any number of the substituted groups up to a substituted group at each position on the ring, with one or two substituted groups being preferred. The various substituted groups can be the same or different.

The reaction conditions are the same as set forth above with regard to the formation of the mono- or bis(iodonium salts) using BTOSA and BTHSA. That is, the temperature conditions are from slightly above the freezing point to about the boiling point, etc., the use of a neutral organic solvent, e.g., pH 4.0 to 9.0, etc., pressure from about 0.2 to about 5.0 atmospheres, etc., and the like are all the same and are hereby fully incorporated. Moreover, the molar amount of the mono- or bis(triorganosilyl)heterocyclic compound is generally in slight excess of the Hosia compounds, (formula 3), as noted above, that is, a mole ratio of from about 0.8 to about 5, desirably from about 0.9 to about 2, and preferably about 1.0.

The result of the reaction of the Hosia compound with mono(triorganosilyl)heterocyclic or a mono(-trihalosilyl)heterocyclic is set forth in formula 8.

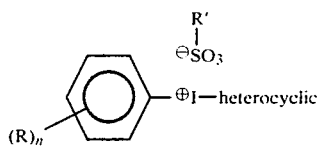

FORMULA 8 where $(R)_n$, R' and heterocyclic are as set forth above.

As apparent from formula 8, the silane substituted group is cleaved during reaction with the heterocyclic compound being attached to the iodine atom. In a similar manner, when a bis(triorganosilyl)heterocyclic or a bis(trihalosilyl)heterocyclic compound is utilized, an iodonium salt generally represented by formula 9 is produced.

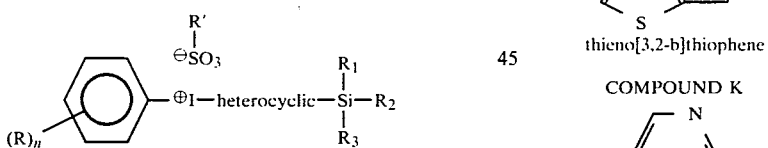

where $(R)_n$, R', $R_1$, $R_2$, $R_3$, and HETEROCYCLIC are as set forth above.

Since the R group can be specifically placed at a specific location with regard to reactants represented by formula 3 as well as to the type of substituent, products set forth in formulas 8 and 9 can generally be made under regiospecific conditions.

The iodonium salts produced by use of the mono- or bis(triorganosilyl)heterocyclic compounds generally have the same uses as the iodonium salts produced utilizing BTOSA or BTHSA compounds. That is, they generally serve as antimicrobial compounds and can be used to resist bacteria, fungi, yeast, and small RNA virus groups, and the like. Another specific use is as upon tooth enamel to prevent tartar buildup thereon.

The various iodonium salts as set forth in formula 9 may further be reacted with another Hosia compound, for example, the same or a different type of compound to yield a bis(iodonium salt). The silicon bond will be cleaved such that the silane group will be replaced by the added Hosia compound. The temperature conditions, reaction, and the like are the same as previously set forth. Accordingly, it can be seen that a very large number of bis(iodonium salts) containing a heterocyclic compound therein can be made.

The chemical formulae of various heterocyclics are set forth below.

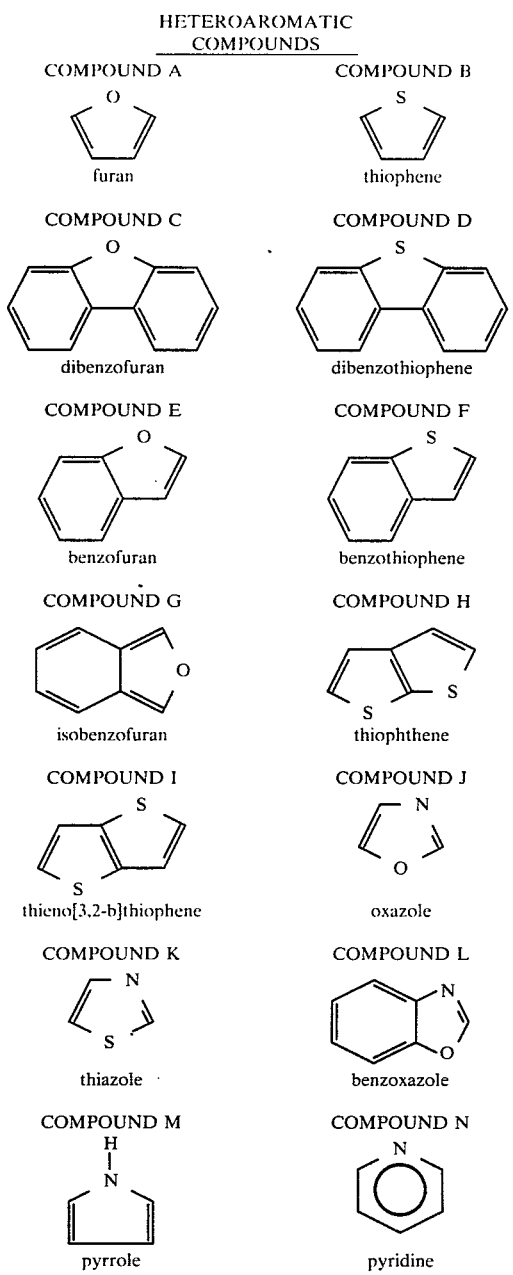

The invention will be better understood by reference to the following examples.

The following starting materials of the present invention are prepared by methods known to the art, for example:

1,4-bis(trimethylsilyl)benzene in a two-step synthesis by the reaction of 1,4-dibromobenzene with n-butyllithium and then by the reaction of 1,4-dilithiobenzene with chlorotrimethylsilane.

1,3-bis(trimethylsilyl)benzene in a two-step synthesis by the reaction of 1,3-dibromobenzene with n-butyllithium and then by the reaction of 1,3-dilithiobenzene with chlorotrimethylsilane.

4,4'-bis(trimethylsilyl)biphenyl in a two-step synthesis by the reaction of 4,4'-dibromobiphenyl with n-butyllithium and then by the reaction of 4,4'-dilithiobiphenyl with chlorotrimethylsilane.

bis(p-trimethylsilylphenyl)ether in a two-step synthesis by the reaction of 4,4'-dibromodiphenyl ether with n-butyllithium and then by the reaction of 4,4'-dilithiodiphenyl ether with chlorotrimethylsilane.

2,5-bis(trimethylsilyl)furan in a two-step synthesis by the reaction of furan with n-butyllithium and then by the reaction of 2,5-dilithiofuran with chlorotrimethylsilane.

2,5-bis(trimethylsilyl)thiophene in a two-step synthesis by the reaction of thiophene with n-butyllithium and then by the reaction of 2,5-dilithiothiophene with chlorotrimethylsilane.

2-furyltrimethylsilane in a two-step synthesis by the reaction of furan with n-butyllithium and then by the reaction of 2-lithiofuran with chlorotrimethylsilane.

4-trimethylsilyl furan in a two-step synthesis by the reaction of dibenzofuran with n-butyllithium and then by the reaction of 2-lithiodibenzofuran with chlorotrimethylsilane.

[hydroxy(tosyloxy)iodo]benzene by the reaction of (diacetoxyiodo)benzene with p-toluenesulfonic acid monohydrate.

[hydroxy(tosyloxy)iodo]-o-toluene by the reaction of (diacetoxyiodo)-o-toluene with p-toluenesulfonic acid monohydrate.

[hydroxy(tosyloxy)iodo]-p-toluene by the reaction of (diacetoxyiodo)-p-toluene with p-toluenesulfonic acid monohydrate.

[hydroxy(tosyloxy)iodo]-p-chlorobenzene by the reaction of 1-chloro-4-iodobenzene with [hydroxy(tosyloxy)iodo]-o-toluene.

[hydroxy(tosyloxy)iodo]-p-bromobenzene by the reaction of 1-bromo-4-iodobenzene with [hydroxy(tosyloxy)iodo]-o-toluene.

(diacetoxyiodo)-o-toluene by the reaction of o-iodotoluene with 40 percent peracetic acid.

(diacetoxyiodo)-m-toluene by the reaction of m-iodotoluene with 40 percent peracetic acid.

(diacetoxyiodo)-p-toluene by the reaction of p-iodotoluene with 40 percent peracetic acid.

EXAMPLE 1

Reaction of 4,4'-bis(trimethylsilylbiphenyl with [hydroxy(tosyloxy)iodo]benzene

To a slurry of 4,4'-bis(trimethylsilyl)biphenyl (1.00 g, 3.35 mmol) in acetonitrile (35 ml) was added [hydroxy(tosyloxy)iodo]benzene (1.31 g, 3.34 mmol). The mixture was refluxed on a steam bath for 4.22 hour and then filtered into 100 ml of ether. The precipitate which formed was isolated in two fractions; 0.419 g, 0.125 g. Ether (about 150 ml) was added to the filtrate which had evaporated to a small volume and two more crops of solid were obtained; 0.316 g, 0.040 g. The total yield of crude product was 0.900 g, (45.0 percent).

For recrystallization 0.666 g of the crude product was dissolved in methanol (ca. 11 ml) and filtered. Ether (50 ml) was slowly added so that a cloud point was achieved. Crystallization began and more ether (50 ml) was added. Ten to fifteen minutes later, the solid was isolated by filtration to give 0.337 g of (4-trimethylsilylbiphenyl)phenyliodonium tosylate; mp 206–8 C. (dec. to a light tan colored liquid). The filtrate evaporated to dryness, leaving behind 0.17 g product. A 0.145 g portion of this was recrystallized from methanol and ether to obtain 0.69 g. Overall percent yield: 27.4%; $^1$H NMR (CDCl$_3$) δ 0.27 (s, 9H), δ 2.25 (s, 3H), δ 6.95–8.25 (m, 17H).

Anal. Calcd for $C_{28}H_{29}O_3ISiS$: C, 56.00; H, 4.87; I, 21.13. Found: C, 56.24; H, 4.83; I, 20.98.

EXAMPLE 2

Reaction of bis(p-trimethylsilylphenyl)ether with one equivalent of [hydroxy(tosyloxy)iodo]benzene To a solution of bis(p-trimethylsilylphenyl)ether (1.55 g, 0.00493 mol) in acetonitrile (20 ml) was added [hydroxy(tosyloxy)iodo]benzene (1.87 g, 0.00477 mol). The solution was vigorously refluxed until the [hydroxy(tosyloxy)iodo]benzene had dissolved and then refluxed more gently for 5.17 hours. The solvent was removed on a rotary evaporator and a yellow oil (3.39 g) remained. The oil did not crystallize upon the addition of ether. Then, it was transferred to a 250 ml beaker (the last portions being transferred with the aid of methanol). The methanol was allowed to evaporate. The oil was crystallized by first dissolving it in methanol (ca. 10 ml), and then adding sufficient ether to achieve the cloud point. A few hours were required for crystallization to occur, then the mixture was filtered. Addition of ether to the filtrate caused more precipitation; the filtrate was filtered. This process was repeated three or four times over a 2-day period. Approximately 200 ml total of ether was used in these processes. The weight of white crystalline [4-(4-trimethylsilylphenoxy)phenyl]phenyliodonium tosylate was 1.44 g (49.0%); mp 157–159.5 C. The entire 1.44 g portion was then redissolved in 4.4 ml of methanol and recrystallized by the addition of 50 ml of ether and 0.97 g of a powdery product, melting at 159–161.5 C. was obtained. An ethanol/water mixture was found to be a superior recrystallization solvent. A 0.79 g portion was dissolved in 5.0 ml of 95 percent ethanol by gentle heating. The solution was filtered, the funnel rinsed with 3.3 ml of 95 percent ethanol, and 9 ml of water was added to the filtrate to achieve a cloud point. Ultimately, 0.55 g (23.0 percent yield overall) of fine shiny white needles crystallized out of solution: mp 173.5–175 C.; $^1$H NMR (DMSO-d$_6$) δ 0.21 (s, 9H), δ 2.18 (s, 3H), δ 6.79–8.24 (m, 17H).

Anal. Calcd for $C_{28}H_{29}O_4ISiS$: C, 54.54; H, 4.74; I, 20.58. Found: C, 54.49; H, 4.81; I, 20.57.

EXAMPLE 3

Reaction of p-(trimethylsilylphenyl)ether with two equivalents of [hydroxy(tosyloxy)iodo]benzene To a solution of p-bis(trimethylsilylphenyl)ether (1.52 g, 4.84 mmol) in acetonitrile (25 ml) was added [hydroxy(tosyloxy)iodo]benzene (3.78 g, 9.64 mmol). The reaction mixture was first vigorously refluxed to promote the dissolution of [hydroxy(tosyloxy)iodo]benzene and then refluxed more gently for a total of 5.17 hours. The solvent was removed on a rotary evaporator and yielded a thick yellow oil (5.42 g). The oil crystallized from methanol (ca. 20 ml) and ether (ca. 51 ml) and was filtered to obtain a white powder weighing 1.08 g, (24.7 percent yield); mp 178–85. A recrystallization of 0.94 g from methanol (10 ml) and ether (25 ml) yielded 0.730 g, (19.2 percent); mp 185–7.

Anal. Calcd for $C_{38}H_{32}O_7I_2S_2$: C, 49.68; H, 3.51; I, 27.63. Found: C, 49.49; H, 3.52; I, 28.78.

Recrystallization was repeated twice in order to improve the analysis. A recrystallization of 0.647 g from methanol (4 ml) and ether (3.5 ml) yielded the white product (0.440 g, 13.0 percent); mp 191–197. Then, 0.35 g of this was recrystallized from methanol (6.2 ml) and ether (25 ml) to yield after filtration 0.26 g, (9.70 percent); mp 195°–8° C.

Anal. Calcd for $C_{38}H_{32}O_7I_2S_2$: C, 49.68; H, 3.51; I, 27.63. Found: C, 49.82; H, 3.61; I, 28.34, and I, 28.11.

EXAMPLE 4

Reaction of 2,5-bis(trimethylsilyl)thiophene with [hydroxy(tosyloxy)iodo]benzene To a solution of 2,5-bis(trimethylsilyl)thiophene (8.60 g, 376 mmol) in acetonitrile (100 ml) is added [hydroxy(tosyloxy)iodo]benzene (14.75 g, 376. mmol). The reaction mixture is refluxed for 4½ hours. In order to separate any small amount of solid from the solution, the mixture is fluted filtered. The solution is poured into anhydrous diethyl ether (300 ml) and phenyl-(5-trimethylsilyl-2-thienyl)iodonium tosylate (15.53 g, 76.8 percent, mp 173–5 C. dec.) precipitates in the appearance of wet tissue. A 15.15 g portion is recrystallized from reagent acetone (1.5 L) to obtain 11.45 g (58.0 percent overall) of white product: mp 174.5–176.8 C. dec; $^1$H NMR (CDCl$_3$)- δ 0.30 (s, 9H), δ 2.25 (s, 3H), δ 6.78–7.98 (m, 11H).

Anal. Calcd for $C_{20}H_{23}O_3S_2ISi$: C, 45.28; H, 4.37; I, 23.92. Found: C, 45.08; H, 4.36; I, 23.96.

EXAMPLE 5

Reaction of 2,5-bis(trimethylsilyl)furan with [hydroxy(tosyloxy)iodo]benzene

To a solution of 2,5-bis(trimethylsily)furan (6.32 g, 29.8 mmol) in acetonitrile (65 ml) was added [hydroxy(tosyloxy)iodo]benzene (11.67 g, 29.8 mmol). The mixture was refluxed on a steam bath for 2.67 hours and then pipetted into technical grade ether (900 ml). The precipitate (6.32 g, 41.3 percent yield; mp 157° C., dec. to a black liquid) which formed was filtered, rinsed with ether on the Buchner funnel, and dried. A 5.94 g portion was treated with charcoal and recrystallized from reagent acetone (200 ml) to yield a 1.91 g fraction and a 1.62 g fraction (24.5 percent overall) of phenyl(5-trimethylsilyl-2-furyl)iodonium tosylate. The melting point decreased to 151°–2° C., dec. to a black liquid. The product appears as a white, fibrous asbestos-looking material and also looks similar to fluffy, shredded tissue. $^1$H NRM (CDCL$_3$) δ 0.27 (s, 9H), δ 2.32 (s, 3H), δ 6.13–800 (m, 11H).

Anal. Calcd for $C_{20}H_{23}O_4ISSi$: C, 46.69; H, 4.51; I, 24.67. Found: C, 46.86; H, 4.51, I, 24.92.

EXAMPLE 6

In a similar manner, the following compounds of the present invention were prepared in neutral organic solvents, at temperatures set forth in this specification:

phenyl(4-trimethylsilylphenyl)iodonium tosylate (mp 174–176 C., dec., m.w. 524.50) by the reaction of 1,4-bis(trimethylsilyl)benzene with [hydroxy(tosyloxy)iodo]benzene; the corresponding iodide (mp 158–160 C., dec.).

phenyl(3-trimethylsilylphenyl)iodonium tosylate (m.w. 524.50) by the reaction of 1,3-bis(trimethylsilyl)benzene with [hydroxy(tosyloxy)iodo]benzene.

(2-methylphenyl)(5-trimethylsilyl-2-furyl)iodonium tosylate (mp 148–9 dec. to black liquid; m.w. 528.48) by the reaction of 2,5-bis(trimethylsilyl)furan with [hydroxy(tosyloxy)iodo]-o-toluene.

(3-methylphenyl)(5-trimethylsilyl-2-furyl)iodonium tosylate (m.w. 528.48) by the reaction of 2,5-bis(trimethylsilyl)furan with [hydroxy(tosyloxy)iodo]-m-toluene.

(4-methylphenyl)(5-trimethylsilyl-2-furyl)iodonium tosylate (m.w. 528.48) by the reaction of 2,5-bis(trimethylsilyl)furan with [hydroxy(tosyloxy)iodo]-p-toluene.

(4-chlorophenyl)(5-trimethylsilyl-2-furyl)iodonium tosylate (m.w. 548.90) by the reaction of 2,5-bis(trimethylsilyl)furan with [hydroxy(tosyloxy)iodo]-p-chlorobenzene.

(4-bromophenyl)(5-trimethylsilyl-2-furyl)iodonium tosylate (m.w. 593.36) by the reaction of 2,5-bis(trimethylsilyl)furan with [hydroxy(tosyloxy)iodo]-p-bromobenzene.

2-furylphenyliodonium tosylate (m.w. 442.27) by the reaction of 2-furyltrimethylsilane with [hydroxy(tosyloxy)iodo]benzene.

(4-dibenzofuryl)phenyliodonium tosylate (m.w. by the reaction of 4-trimethylsilyldibenzofuran with [hydroxy(tosyloxy)iodo]-o-toluene.

EXAMPLE 7

In a similar manner, the following compounds of the present invention were prepared in neutral organic solvents at temperatures set forth in this specification.

| R | Het | R' | time, hr. | % Yield |
|---|---|---|---|---|
| H | O (furan) | —SiMe$_3$ | 2.67 | 41.3% crude<br>24.5% recryst. |
| o-Me | O (furan) | —SiMe$_3$ | 2.5 | 43.0% crude |
| m-Me | O (furan) | —SiMe$_3$ | 2 | 41.6% crude |
| p-Me | O (furan) | —SiMe$_3$ | 2.5 | 22.4% crude |
| p-Cl | O (furan) | —SiMe$_3$ | 2 | 23.3% crude |

(15° to 90° C.)

-continued

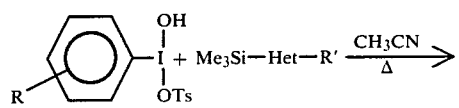

| R | Het | R' | time, hr. | % Yield |
|---|---|---|---|---|
| p-Br | O (furan) | —SiMe₃ | 2.5 | 9.2% crude |
| H | O (furan) | —H | 3 | 11.3% crude |
| H | S (thiophene) | —SiMe₃ | 4.5 | 76.8% crude / 58.0% recryst. |
| o-CH₃ | (dimethylbiphenyl-O) | —H | 4 | 20.0% crude |

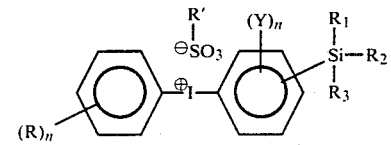
(15° to 90° C.)

EXAMPLE 8

Similarly, the following compounds were made in neutral organic solvents at temperatures set forth in this specification.

| n | Ar | Y | time, hr. | % Yield |
|---|---|---|---|---|
| 2 | (p-phenylene) | —SiMe₃ | 8 | 10% crude |
| 1 | (m-phenylene) | —SiMe₃ | 4.5 | 51.8% crude / 11.3% recryst. |
| 1 | (biphenylene) | —SiMe₃ | 4.22 | 45.0% crude / 27.4% recryst. |
| 1 | (diphenyl ether) | —SiMe₃ | 5.17 | 49.0% crude / 23.0% recryst. |
| 2 | (diphenyl ether) | —I⁺Ph OTs⁻ | 5.17 | 24.7% crude / 9.7% recryst. |

While having described the best mode and preferred embodiments of the present invention, in accordance with the patent statutes, the scope of the invention is not to be limited thereto, the invention being measured by the attached claims.

What is claimed is:

1. An iodonium salt, comprising: a compound having the formula

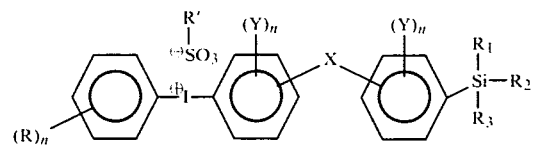

or the formula where n of $(R)_n$ is from 1 to 5,
where R can be benzo, a halo, an alkyl having from 1 to 20 carbon atoms, a cycloalkyl having from 3 to 20 carbon atoms, an aryl having from 6 to 40 carbon atoms, a halogen substituted aryl wherein said aryl has from 6 to 40 carbon atoms, a naphthyl, a halo substituted naphthyl, an alkyl substituted naphthyl wherein said alkyl has from 1 to 20 carbon atoms, a cycloalkyl substituted naphthyl wherein said cycloalkyl has from 3 to 20 carbon atoms, a hetero atom substituent substituted on an aryl with said aryl having from 6 to 40 carbon atoms, said hetero atoms selected from the group consisting of CN, $NO_2$, COOH, CHO, OH, an alkoxy having from 1 to 5 carbon atoms, an aryloxy having from 6 to 30 carbon atoms, and combinations thereof; a pyridinyl, alpha or beta furyl, thienyl, and combinations thereof;

wherein said R' is hydrogen, an alkyl having from 1 to 20 carbon atoms, an aryl having from 6 to 40 carbon atoms, a halogen substituted aryl wherein said aryl has from 6 to 40 carbon atoms, a hetero atom substituent substituted on an aryl having from 6 to 40 carbon atoms, said hetero atom substituent selected from the group consisting of CN, $NO_2$, COOH, CHO, an alkoxy having from 1 to 6 carbon atoms, an aryloxy having from 6 to 30 carbon atoms, and combinations thereof;

wherein Y is hydrogen, an alkyl having from 1 to 5 carbon atoms, an aryl having from 6 to 12 carbon atoms, a halo, and a hetero group selected from the group consisting of $NO_2$, CN, COOH, CHO, OH, and combinations thereof;

wherein $R_1$, $R_2$, and $R_3$ is hydrogen, an alkyl having from 1 to 5 carbon atoms, a halo, an aryl having from 6 to 24 atoms, an alkoxy having from 1 to 5 carbon atoms;

wherein X is O, NH, S,

Sn, SO, $SO_2$, a ketone group, N-R''' where R''' is an alkyl having from 0 to 5 carbon atoms or an aryl having from 6 to 12 carbon atoms, $-(CH_2)_n-$ where n is from 0 to 10, $-CR'_2-C$ where R' is an alkyl having from 0 to 5 carbon atoms, —C aryl (n) wherein said aryl has from 6 to 12 carbon atoms, and n is from 1 to 10; a $-SiR'''_{2(n)}$ where said R''' is an alkyl having from 0 to 5 carbon atoms or an aryl having from 6 to 12 carbon atoms, and n is from 1 to 10, $-(Si)_n-$ where n is from 1 to 10, a phenylene repeating group having from 1 to 10 units.

2. An iodonium salt according to claim 1, wherein said R alkyl has from 1 to 5 carbon atoms, wherein said R aryl has from 6 to 20 carbon atoms, wherein X is O, NH, S, or $-(CH_2)_n-$ wherein n is 0 to 10.

3. An iodonium salt according to claim 2, wherein said n of said $(R)_n$ is 1 or 2, wherein said R is an alkyl having from 1 to 20 carbon atoms, an aryl having from 6 to 40 carbon atoms, halo, wherein said R' is said aryl, said halo subsituted aryl and said hetero atom substituted aryl, wherein Y is hydrogen, and wherein $R_1$, $R_2$, and $R_3$ is methyl, chloro, or a phenyl.

4. An iodonium salt according to claims 1, 2, or 3, wherein R' is an aryl having from 6 to 40 carbon atoms, or an alkyl having from 1 to 10 carbon atoms.

5. An iodonium salt according to claim 4, wherein said R' is tolyl.

6. An iodonium salt, comprising:
a compound having the formula

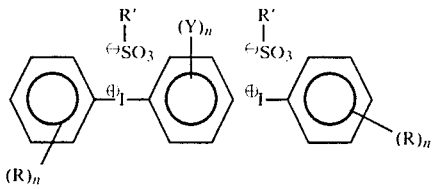

or the formula

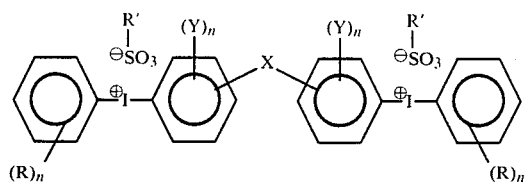

where n of $(R)_n$ is from 1 to 5, where R can be benzo, a halo, an alkyl having from 1 to 20 carbon atoms, a cycloalkyl having from 4 to 20 carbon atoms, an aryl having from 6 to 40 carbon atoms, a halogen substituted aryl wherein said aryl has from 6 to 40 carbon atoms, a naphthyl, a halo substituted naphthyl, an alkyl substituted naphthyl wherein said alkyl has from 1 to 20 carbon atoms, a cycloalkyl substituted naphthyl wherein said cycloalkyl has from 3 to 20 carbon atoms, a hetero atoms substituent on an aryl with said aryl having from 6 to 40 carbon atoms, said hetero atom selected from the group consisting of CN, $NO_2$, COOH, CHO, OH, an alkoxy having from 1 to 5 carbon atoms, an aryloxy having from 6 to 30 carbon atoms, and combinations thereof; a pyridinyl, alpha or beta furyl, alpha or beta thienyl, and combinations thereof;

wherein said R' is hydrogen, an alkyl having from 1 to 20 carbon atoms, a halogen substituted aryl wherein said aryl has from 6 to 40 carbon atoms, a hetero atoms substituent substituted on an aryl having from 6 to 40 carbon atoms, said hetero atom substituent selected from the group consisting of CN, $NO_2$, COOH, CHO, an alkoxy having from 1 to 6 carbon atoms, an aryloxy having 6 to 30 carbon atoms, and combinations thereof;

wherein Y is hydrogen, an alkyl having from 1 to 5 carbon atoms, an aryl having from 6 to 12 carbon atoms, a halo, and a hetero group selected from the group consisting of $NO_2$, CN, COOH, CHO, OH, and combinations thereof;

wherein X is O, NH, S,

Sn, SO, $SO_2$, a ketone group, N—R''' where R''' is an alkyl having from 0 to 5 carbon atoms or an aryl having from 6 to 12 carbon atoms, $-(CH_2)_n-$ where n is from 0 to 10, $-CR'_2-C$ where R' is an alkyl having from 0 to 5 carbon atoms, —C aryl (n)

wherein said aryl has from 6 to 12 carbon atoms, and n is from 1 to 10; a —SiR'''$_{2(n)}$ where said R''' is an alkyl having from 0 to 5 carbon atoms or an aryl having from 6 to 12 carbon atoms, and n is from 1 to 10, ⟨Si⟩$_n$ where n is from 1 to 10, a

wherein n is from 1 to 10 units, a phenylene repeating group having from 1 to 10 units.

7. An iodonium salt according to claim 6, wherein said R alkyl has from 1 to 5 carbon atoms, wherein said R aryl has from 6 to 20 carbon atoms, wherrein X is O, NH, S, or —CH$_2$—$_n$ wherein n is 0 to 10.

8. An iodonium salt according to claim 7,
wherein said n of said (R)$_n$ is 1 or 2, wherein said R is an alkyl having from 1 to 20 carbon atoms, an aryl having from 6 to 40 carbon atoms, a halo,
wherein said R' is said aryl, said halo substituted aryl and said hetero atom substituted aryl, and
wherein Y is hydrogen.

9. An iodonium salt according to claim 6, 7, or 8, wherein R' is an aryl having from 6 to 40 carbon atoms, or an alkyl having from 1 to 10 carbon atoms.

10. An iodonium salt according to claim 9, wherein said R' is tolyl.

11. An iodonium salt, comprising:
a compound having the formula

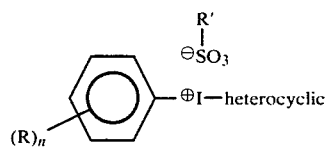

or a compound having the formula

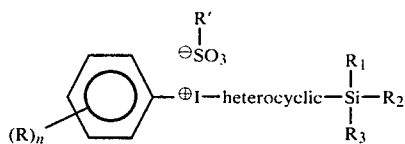

or a compound having the formula

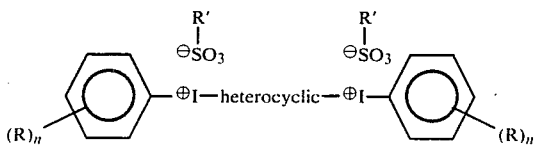

where n of (R)$_n$ is from 1 to 5, where R can be benzo, a halo, an alkyl having from 1 to 20 carbon atoms, a cycloalkyl having from 3 to 20 carbon atoms, an aryl having from 6 to 40 carbon atoms, a halogen substituted aryl wherein said aryl has from 6 to 40 carbon atoms, a naphthyl, a halo substituted naphthyl, an alkyl substituted naphthyl wherein said alkyl has from 1 to 20 carbon atoms, a cycloalkyl substituted naphthyl wherein said cycloalkyl has from 3 to 20 carbon atoms, a hetero atoms substituent substituted on an aryl with said aryl having from 6 to 40 carbon atoms, said hetero atoms selected from the group consisting of CN, NO$_2$, COOH, CHO, OH, an alkoxy having from 1 to 5 carbon atoms, an aryloxy having from 6 to 30 carbon atoms, and combinations thereof, a pyridinyl, alpha or beta furyl, alpha or beta thienyl, and combinations thereof;

wherein said R' is hydrogen, an alkyl having from 1 to 20 carbon atoms, an aryl having from 6 to 40 carbon atoms, a halogen substituted aryl wherein said aryl has from 6 to 40 carbon atoms, a hetero atom substituent substituted on an aryl having from 6 to 40 carbon atoms, said hetero atoms substituent selected from the group consisting of CN, NO$_2$, COOH, CHO, an alkoxy having from 1 to 6 carbon atoms, an aryloxy having from 6 to 20 carbon atoms, and combinations thereof;

wherein R$_1$, R$_2$, and R$_3$ is hydrogen, an alkyl having from 1 to 5 carbon atoms, a halo, an aryl having from 6 to 24 atoms, an alkoxy having from 1 to 5 carbon atoms; and wherein said heterocyclic compound is selected from the group consisting of furan, thiophene, dibenzofuran, dibenzothiophthene, thieno[3,2-b]thiophene, oxazole, thiazole, benzoxazole, pyrrole, and pyridine.

12. An iodonium salt according to claim 11, wherein said R alkyl has from 1 to 5 carbon atoms, wherein said R aryl has from 6 to 20 carbon atoms.

13. An iodonium salt according to claim 12,
wherein said R is an alkyl having from 1 to 20 carbon atoms, an aryl having from 6 to 40 carbon atoms, halo,
wherein said R' is said aryl, said halo substituted aryl and said hetero atom substituted aryl, and
wherein R$_1$, R$_2$, and R$_3$ is methyl, chloro, or a phenyl.

14. An iodonium salt according to claims 11, 12, or 13, wherein R' is an aryl having from 6 to 40 carbon atoms, or an alkyl having from 1 to 10 carbon atoms.

15. An iodonium salt according to claim 14, wherein R' is tolyl.

16. An iodonium salt, comprising:
a compound having the formula

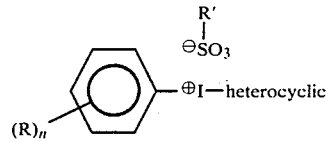

or a compound having the formula

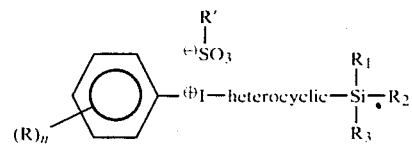

or a compound having the formula

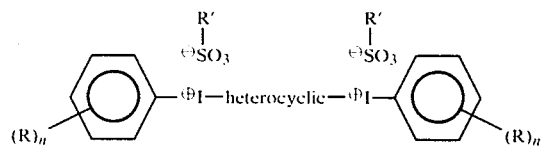

where n of (R)$_n$ is from 1 to 5, where R can be benzo, a halo, an alkyl having from 1 to 20 carbon atoms, a cycloalkyl having from 3 to 20 carbon atoms, an aryl having from 6 to 40 carbon atoms, a halogen substituted aryl wherein said aryl has from 6 to 40 carbon atoms, a naphthyl, a halo substituted naphthyl, an alkyl substituted naphthyl wherein said alkyl has from 1 to 20 carbon carbon atoms, a cycloalkyl substituted naphthyl wherein said cycloalkyl has from 3 to 20 carbon atoms, a hetero atoms substituent substituted on an aryl with said aryl having from 6 to 40 carbon atoms, said hetero atoms selected from the group consisting of CN, NO$_2$, COOH, CHO, OH, an alkoxy having from 1 to 5 carbon atoms, an aryloxy having from 6 to 30 carbon atoms, and combinations thereof, a pyridinyl, alpha or beta furyl, alpha or beta thienyl, and combinations thereof;

wherein said R' is hydrogen, an alkyl having from 1 to 20 carbon atoms, an aryl having from 6 to 40 carbon atoms, a halogen substituted aryl wherein said aryl has from 6 to 40 carbon atoms, a hetero atom substituent substituted on an aryl having from 6 to 40 carbon atoms, said hetero atoms substituent selected from the group consisting of CN, NO$_2$, COOH, CHO, an alkoxy having from 1 to 6 carbon atoms, an aryloxy having from 6 to 20 carbon atoms, and combinations thereof;

wherein R$_1$, R$_2$ and R$_3$ is hydrogen, an alkyl having from 1 to 5 carbon atoms, a halo, an aryl having from 6 to 24 carbon atoms, an alkoxy having from 1 to 5 carbon atoms; and wherein said heterocyclic compound is selected from the group consisting of dibenzofuran, dibenzothiophthene, thieno[3,2-b]thiophene, oxazole, thiazole, benzoxazole, and pyrrole.

17. An iodonium salt according to claim 16, wherein said R alkyl has from 1 to 5 carbon atoms, and wherein said R aryl has from 6 to 20 carbon atoms.

18. An iodonium salt according to claim 17,
wherein said R is an alkyl having from 1 to 20 carbon atoms, an aryl having from 6 to 40 carbon atoms, halo,
wherein said R' is said aryl, said halo substituted aryl and said hetero atoms substituted aryl; and
wherein R$_1$, R$_2$ and R$_3$ is methyl, chloro, or a phenyl.

19. An iodonium salt according to claim 18, wherein R' is an aryl having from 6 to 40 carbon atoms, or an alkyl having from 1 to 10 carbon atoms.

20. An iodonium salt according to claim 19, wherein R' is tolyl.

* * * * *